US011826106B2

(12) United States Patent
Hart et al.

(10) Patent No.: US 11,826,106 B2
(45) Date of Patent: Nov. 28, 2023

(54) METHOD AND SYSTEM FOR PROVIDING INFORMATION FROM A PATIENT-SPECIFIC MODEL OF BLOOD FLOW

(71) Applicant: HeartFlow, Inc., Redwood City, CA (US)

(72) Inventors: Gregory R. Hart, Hayden Lake, ID (US); John H. Stevens, Palo Alto, CA (US)

(73) Assignee: HeartFlow, Inc., Mountain View, CA (US)

( * ) Notice: Subject to any disclaimer, the term of this patent is extended or adjusted under 35 U.S.C. 154(b) by 429 days.

(21) Appl. No.: 17/075,892

(22) Filed: Oct. 21, 2020

(65) Prior Publication Data
US 2021/0030478 A1 Feb. 4, 2021

Related U.S. Application Data

(63) Continuation of application No. 15/268,031, filed on Sep. 16, 2016, now Pat. No. 10,842,568, which is a
(Continued)

(51) Int. Cl.
*A61B 5/026* (2006.01)
*A61B 34/10* (2016.01)
(Continued)

(52) U.S. Cl.
CPC .............. *A61B 34/10* (2016.02); *A61B 5/021* (2013.01); *A61B 5/026* (2013.01);
(Continued)

(58) Field of Classification Search
CPC ..... A61B 34/10; A61B 5/02007; A61B 5/021; A61B 5/026; A61B 5/0263; A61B 5/055;
(Continued)

(56) References Cited

U.S. PATENT DOCUMENTS

| 5,119,816 A | 6/1992 | Gevins |
| 5,151,856 A | 9/1992 | Halmann et al. |

(Continued)

FOREIGN PATENT DOCUMENTS

| CN | 1820707 | * 8/2006 |
| CN | 1853576 A | 11/2006 |

(Continued)

OTHER PUBLICATIONS

International Search Report dated Oct. 31, 2013 in International Application No. PCT/US2013/040714.
(Continued)

*Primary Examiner* — Kandasamy Thangavelu
(74) *Attorney, Agent, or Firm* — Bookoff McAndrews, PLLC

(57) ABSTRACT

Embodiments include a system for providing blood flow information for a patient. The system may include at least one computer system including a touchscreen. The at least one computer system may be configured to display, on the touchscreen, a three-dimensional model representing at least a portion of an anatomical structure of the patient based on patient-specific data. The at least one computer system may also be configured to receive a first input relating to a first location on the touchscreen indicated by at least one pointing object controlled by a user, and the first location on the touchscreen may indicate a first location on the displayed three-dimensional model. The at least one computer system may be further configured to display first information on the touchscreen, and the first information may indicate a blood flow characteristic at the first location.

20 Claims, 6 Drawing Sheets

Related U.S. Application Data continuation of application No. 14/177,630, filed on Feb. 11, 2014, now Pat. No. 9,517,040, which is a continuation of application No. 14/030,801, filed on Sep. 18, 2013, now Pat. No. 8,706,457, which is a continuation of application No. 13/470,802, filed on May 14, 2012, now Pat. No. 8,548,778.

(51) Int. Cl.

| | | |
|---|---|---|
| *G16B 5/00* | (2019.01) | |
| *A61B 6/00* | (2006.01) | |
| *A61B 5/055* | (2006.01) | |
| *G06T 19/20* | (2011.01) | |
| *G16H 50/50* | (2018.01) | |
| *A61B 5/00* | (2006.01) | |
| *G06F 30/20* | (2020.01) | |
| *G16H 30/20* | (2018.01) | |
| *G06F 3/04815* | (2022.01) | |
| *G06F 3/0488* | (2022.01) | |
| *G06T 17/00* | (2006.01) | |
| *G06T 15/00* | (2011.01) | |
| *A61B 5/021* | (2006.01) | |
| *A61B 5/02* | (2006.01) | |
| *G06F 3/0486* | (2013.01) | |
| *A61B 6/03* | (2006.01) | |
| *A61B 8/06* | (2006.01) | |
| *G06F 3/01* | (2006.01) | |
| *A61B 5/022* | (2006.01) | |

(52) U.S. Cl.
CPC ........ *A61B 5/02007* (2013.01); *A61B 5/0263* (2013.01); *A61B 5/055* (2013.01); *A61B 5/7275* (2013.01); *A61B 5/7278* (2013.01); *A61B 5/748* (2013.01); *A61B 5/7425* (2013.01); *A61B 5/7445* (2013.01); *A61B 6/032* (2013.01); *A61B 6/466* (2013.01); *A61B 6/504* (2013.01); *A61B 6/5217* (2013.01); *A61B 8/06* (2013.01); *G06F 3/017* (2013.01); *G06F 3/0486* (2013.01); *G06F 3/0488* (2013.01); *G06F 3/04815* (2013.01); *G06F 30/20* (2020.01); *G06T 15/00* (2013.01); *G06T 17/00* (2013.01); *G06T 19/20* (2013.01); *G16B 5/00* (2019.02); *G16H 30/20* (2018.01); *G16H 50/50* (2018.01); *A61B 5/022* (2013.01); *A61B 6/03* (2013.01); *A61B 2034/104* (2016.02); *A61B 2576/023* (2013.01); *G06T 2200/04* (2013.01); *G06T 2200/24* (2013.01); *G06T 2210/41* (2013.01); *G06T 2219/2016* (2013.01)

(58) Field of Classification Search
CPC ... A61B 5/7275; A61B 5/7278; A61B 5/7425; A61B 5/7445; A61B 5/748; A61B 6/032; A61B 6/466; A61B 6/504; A61B 6/5217; A61B 8/06; A61B 5/022; A61B 6/03; A61B 2034/104; A61B 2576/023; G06F 3/017; G06F 3/04815; G06F 3/0486; G06F 3/0488; G06F 30/20; G06T 15/00; G06T 17/00; G06T 19/20; G06T 2200/04; G06T 2200/24; G06T 2210/41; G06T 2219/2016; G16B 5/00; G16H 30/20; G16H 50/50; Y02A 90/10
See application file for complete search history.

(56) References Cited

U.S. PATENT DOCUMENTS

| | | |
|---|---|---|
| 5,205,289 A | 4/1993 | Hardy et al. |
| 5,235,510 A | 8/1993 | Yamada et al. |
| 5,582,173 A | 12/1996 | Li |
| 5,682,886 A | 11/1997 | Delp et al. |
| 5,687,208 A | 11/1997 | Bae et al. |
| 5,687,737 A | 11/1997 | Branham et al. |
| 5,729,670 A | 3/1998 | Strumolo et al. |
| 5,740,802 A | 4/1998 | Nafis et al. |
| 5,782,762 A | 7/1998 | Vining |
| 5,825,908 A | 10/1998 | Pieper et al. |
| 5,871,018 A | 2/1999 | Delp et al. |
| 5,920,319 A | 7/1999 | Vining et al. |
| 5,947,899 A | 9/1999 | Winslow et al. |
| 6,026,173 A | 2/2000 | Svenson et al. |
| 6,047,080 A | 4/2000 | Chen et al. |
| 6,083,162 A | 7/2000 | Vining |
| 6,117,087 A | 9/2000 | Kamm et al. |
| 6,169,917 B1 | 1/2001 | Masotti et al. |
| 6,176,838 B1 | 1/2001 | Sase |
| 6,236,878 B1 | 5/2001 | Taylor et al. |
| 6,266,453 B1 | 7/2001 | Hibbard et al. |
| 6,272,366 B1 | 8/2001 | Vining |
| 6,278,460 B1 | 8/2001 | Myers et al. |
| 6,366,800 B1 | 4/2002 | Vining et al. |
| 6,379,041 B1 | 4/2002 | Schuetz et al. |
| 6,381,562 B2 | 4/2002 | Keane |
| 6,442,235 B2 | 8/2002 | Koppe et al. |
| 6,466,205 B2 | 10/2002 | Simpson et al. |
| 6,487,432 B2 | 11/2002 | Slack |
| 6,501,848 B1 | 12/2002 | Carroll et al. |
| 6,606,091 B2 | 8/2003 | Liang et al. |
| 6,628,743 B1 | 9/2003 | Drummond et al. |
| 6,650,724 B2 | 11/2003 | Strobel |
| 6,666,820 B1 | 12/2003 | Poole |
| 6,694,163 B1 | 2/2004 | Vining |
| 6,711,433 B1 | 3/2004 | Geiger et al. |
| 6,718,004 B2 | 4/2004 | Cesmeli |
| 6,720,966 B2 | 4/2004 | Barth et al. |
| 6,793,496 B2 | 9/2004 | Edic et al. |
| 6,801,643 B2 | 10/2004 | Pieper |
| 6,898,453 B2 | 5/2005 | Lee |
| 6,909,913 B2 | 6/2005 | Vining |
| 6,932,842 B1 | 8/2005 | Litschko et al. |
| 6,950,689 B1 | 9/2005 | Willis et al. |
| 6,996,262 B2 | 2/2006 | Li |
| 7,006,955 B2 | 2/2006 | Daft et al. |
| 7,121,832 B2 | 10/2006 | Hsieh et al. |
| 7,149,333 B2 | 12/2006 | Pieper et al. |
| 7,149,564 B2 | 12/2006 | Vining et al. |
| 7,182,602 B2 | 2/2007 | Lakin et al. |
| 7,191,110 B1 | 3/2007 | Charbel et al. |
| 7,229,412 B2 | 6/2007 | Jacob et al. |
| 7,286,866 B2 | 10/2007 | Okerlund et al. |
| 7,302,286 B2 | 11/2007 | Camus et al. |
| 7,321,677 B2 | 1/2008 | Evron et al. |
| 7,327,862 B2 | 2/2008 | Murphy et al. |
| 7,333,643 B2 | 2/2008 | Murphy et al. |
| 7,333,648 B2 | 2/2008 | Edic et al. |
| 7,343,196 B2 | 3/2008 | Okerlund et al. |
| 7,356,367 B2 | 4/2008 | Liang et al. |
| 7,369,691 B2 | 5/2008 | Kondo et al. |
| 7,371,067 B2 | 5/2008 | Anderson et al. |
| 7,462,153 B2 | 12/2008 | Bostian et al. |
| 7,474,776 B2 | 1/2009 | Kaufman et al. |
| 7,505,551 B2 | 3/2009 | Grass et al. |
| 7,526,112 B2 | 4/2009 | Murphy et al. |
| 7,536,042 B2 | 5/2009 | Murphy et al. |
| 7,539,529 B2 | 5/2009 | Schmitt et al. |
| 7,542,595 B2 | 6/2009 | Moreau-Gobard |
| 7,574,026 B2 | 8/2009 | Rasche et al. |
| 7,646,900 B2 | 1/2010 | Movassaghi et al. |
| 7,646,901 B2 | 1/2010 | Murphy et al. |
| 7,689,014 B2 | 3/2010 | Abovitz et al. |
| 7,693,563 B2 | 4/2010 | Suresh et al. |
| 7,725,164 B2 | 5/2010 | Suurmond et al. |

(56) References Cited

U.S. PATENT DOCUMENTS

| | | |
|---|---|---|
| 7,725,165 B2 | 5/2010 | Chen et al. |
| 7,738,626 B2 | 6/2010 | Weese et al. |
| 7,739,090 B2 | 6/2010 | Charbel et al. |
| 7,742,629 B2 | 6/2010 | Zarkh et al. |
| 7,747,055 B1 | 6/2010 | Vining et al. |
| 7,751,984 B2 | 7/2010 | Tang |
| 7,773,719 B2 | 8/2010 | Galant et al. |
| 7,773,785 B2 | 8/2010 | Murphy et al. |
| 7,792,565 B2 | 9/2010 | Vining |
| 7,792,593 B2 | 9/2010 | Rahn et al. |
| 7,805,177 B2 | 9/2010 | Chen et al. |
| 7,813,785 B2 | 10/2010 | Okerlund et al. |
| 7,853,310 B2 | 12/2010 | Vining et al. |
| 8,157,742 B2 | 4/2012 | Taylor |
| 8,311,791 B1 | 11/2012 | Avisar |
| 2002/0002447 A1 | 1/2002 | Keane |
| 2002/0035458 A1 | 3/2002 | Kim et al. |
| 2002/0072880 A1* | 6/2002 | Svanerudh ............ A61B 5/0215 702/189 |
| 2002/0120431 A1 | 8/2002 | Keane |
| 2003/0023266 A1 | 1/2003 | Borillo et al. |
| 2003/0123606 A1 | 7/2003 | Mollus et al. |
| 2003/0204160 A1 | 10/2003 | Kamm et al. |
| 2004/0034309 A1 | 2/2004 | Pullan et al. |
| 2004/0049115 A1 | 3/2004 | Murphy et al. |
| 2004/0064298 A1 | 4/2004 | Levine |
| 2004/0153128 A1 | 8/2004 | Suresh et al. |
| 2004/0176678 A1 | 9/2004 | Murphy et al. |
| 2004/0225213 A1 | 11/2004 | Wang et al. |
| 2005/0010105 A1 | 1/2005 | Sra |
| 2005/0018885 A1 | 1/2005 | Chen et al. |
| 2005/0043609 A1 | 2/2005 | Murphy et al. |
| 2005/0131663 A1 | 6/2005 | Bangs et al. |
| 2005/0272992 A1 | 12/2005 | O'Donnell et al. |
| 2006/0025681 A1 | 2/2006 | Abovitz et al. |
| 2006/0142984 A1 | 6/2006 | Weese et al. |
| 2006/0166176 A1 | 7/2006 | Lakin et al. |
| 2006/0171585 A1 | 8/2006 | Rinck et al. |
| 2006/0173283 A1 | 8/2006 | Axelsson et al. |
| 2006/0235669 A1 | 10/2006 | Charbel et al. |
| 2006/0239528 A1 | 10/2006 | Camus et al. |
| 2006/0241445 A1 | 10/2006 | Altmann et al. |
| 2006/0241461 A1 | 10/2006 | White et al. |
| 2006/0241465 A1 | 10/2006 | Huennekens et al. |
| 2006/0253024 A1 | 11/2006 | Altmann et al. |
| 2006/0278245 A1 | 12/2006 | Gan |
| 2007/0014452 A1 | 1/2007 | Suresh et al. |
| 2007/0041490 A1 | 2/2007 | Jha et al. |
| 2007/0078325 A1 | 4/2007 | Fulmaono et al. |
| 2007/0219448 A1 | 9/2007 | Selp et al. |
| 2007/0231779 A1 | 10/2007 | Santhanam et al. |
| 2007/0238999 A1 | 10/2007 | Specht |
| 2007/0293936 A1 | 12/2007 | Dobak, III |
| 2008/0004508 A1 | 1/2008 | Sun et al. |
| 2008/0020362 A1 | 1/2008 | Cotin et al. |
| 2008/0040087 A1 | 2/2008 | Watrous |
| 2008/0118122 A1 | 5/2008 | Sirohey et al. |
| 2008/0177172 A1 | 7/2008 | John et al. |
| 2008/0205722 A1 | 8/2008 | Schaefer et al. |
| 2008/0208068 A1 | 8/2008 | Robertson et al. |
| 2008/0221439 A1 | 9/2008 | Iddan et al. |
| 2008/0228086 A1 | 9/2008 | Ilegbusi et al. |
| 2008/0262346 A1 | 10/2008 | Assis et al. |
| 2008/0262814 A1 | 10/2008 | Zheng et al. |
| 2008/0269611 A1 | 10/2008 | Pedrizzetti et al. |
| 2008/0270095 A1 | 10/2008 | Lombaert et al. |
| 2008/0275336 A1 | 11/2008 | Deschamps et al. |
| 2008/0294038 A1 | 11/2008 | Weese et al. |
| 2008/0317310 A1 | 12/2008 | Suresh et al. |
| 2008/0319308 A1 | 12/2008 | Tang |
| 2009/0016483 A1 | 1/2009 | Kawasaki et al. |
| 2009/0054774 A1 | 2/2009 | Njemanze |
| 2009/0150184 A1 | 6/2009 | Spahn |
| 2009/0156933 A1 | 6/2009 | Gerard et al. |
| 2009/0161938 A1 | 6/2009 | Shekhar et al. |
| 2009/0177454 A1 | 7/2009 | Bronstein et al. |
| 2009/0281423 A1 | 11/2009 | Sirohey et al. |
| 2009/0281434 A1 | 11/2009 | Messerges |
| 2009/0292206 A1 | 11/2009 | Sato |
| 2009/0310840 A1 | 12/2009 | Mohamed et al. |
| 2009/0324052 A1 | 12/2009 | Nowinski |
| 2010/0017171 A1 | 1/2010 | Spilker et al. |
| 2010/0036269 A1 | 2/2010 | Ferren et al. |
| 2010/0053209 A1 | 3/2010 | Rauch et al. |
| 2010/0070249 A1 | 3/2010 | Ionasec et al. |
| 2010/0081917 A1 | 4/2010 | Zhang et al. |
| 2010/0086099 A1 | 4/2010 | Kuzmanovic |
| 2010/0130878 A1* | 5/2010 | Lasso ..................... G16Z 99/00 703/2 |
| 2010/0152570 A1 | 6/2010 | Navab |
| 2010/0156898 A1 | 6/2010 | Voros et al. |
| 2010/0183206 A1 | 7/2010 | Carlsen et al. |
| 2010/0189337 A1 | 7/2010 | Jandt et al. |
| 2010/0214438 A1 | 8/2010 | Hayashi et al. |
| 2010/0222671 A1 | 9/2010 | Cohen et al. |
| 2010/0241404 A1 | 9/2010 | Taylor et al. |
| 2010/0265251 A1 | 10/2010 | Vining et al. |
| 2010/0266176 A1 | 10/2010 | Masumoto et al. |
| 2010/0272315 A1 | 10/2010 | Tsin et al. |
| 2010/0280352 A1 | 11/2010 | Ionasec et al. |
| 2010/0298719 A1 | 11/2010 | Kock et al. |
| 2010/0309228 A1 | 12/2010 | Mattos et al. |
| 2010/0312094 A1* | 12/2010 | Guttman ................ A61B 34/10 600/411 |
| 2010/0328305 A1 | 12/2010 | Vining |
| 2011/0130651 A1 | 6/2011 | Chen et al. |
| 2011/0152599 A1 | 6/2011 | Bokerlya et al. |
| 2011/0170752 A1 | 7/2011 | Martin et al. |
| 2011/0201915 A1 | 8/2011 | Gogin et al. |
| 2011/0216888 A1 | 9/2011 | Bhasin et al. |
| 2011/0293163 A1 | 12/2011 | Kargar et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0084064 A1* | 4/2012 | Dzenis ................... G16H 50/50 703/11 |
| 2012/0095357 A1 | 4/2012 | Tran |
| 2012/0150516 A1 | 6/2012 | Taylor et al. |
| 2012/0215510 A1 | 8/2012 | Metaxas |
| 2013/0132054 A1 | 5/2013 | Sharma et al. |
| 2013/0340060 A1 | 12/2013 | DiRico et al. |
| 2014/0121524 A1 | 5/2014 | Chiang et al. |
| 2014/0157210 A1 | 6/2014 | Katz et al. |

FOREIGN PATENT DOCUMENTS

| | | |
|---|---|---|
| CN | 102018511 A | 4/2011 |
| CN | 102346811 A | 2/2012 |
| CN | 102387747 A | 3/2012 |
| EP | 0 559 919 | 9/1993 |
| EP | 1 182 619 | 2/2002 |
| EP | 1 225 541 | 7/2002 |
| EP | 1 482 470 | 12/2004 |
| EP | 1 492 071 | 12/2004 |
| EP | 0 961 993 | 2/2005 |
| EP | 1 171 759 | 11/2006 |
| EP | 1 717 758 | 11/2006 |
| EP | 1 961 384 | 8/2008 |
| EP | 1 967 140 | 9/2008 |
| EP | 2 028 608 | 2/2009 |
| EP | 2 138 091 | 12/2009 |
| EP | 2 302 594 | 3/2011 |
| EP | 2 302 595 | 3/2011 |

(56) References Cited

FOREIGN PATENT DOCUMENTS

| | | | |
|---|---|---|---|
| EP | 2 302 596 | 3/2011 | |
| JP | 2002-534204 | 10/2002 | |
| JP | 2007079959 | 7/2003 | |
| JP | 2003-245360 | 9/2003 | |
| JP | 2004513736 A | 5/2004 | |
| JP | 2007-079959 | 3/2007 | |
| JP | 2008-512171 | 4/2008 | |
| JP | 2008-526387 | 7/2008 | |
| JP | 2008302212 A * | 12/2008 | ............ A61B 6/505 |
| JP | 2009-070491 | 4/2009 | |
| JP | 2009-515602 | 4/2009 | |
| JP | 2009517177 A * | 4/2009 | ............... G06T 7/38 |
| JP | 2011062566 A * | 3/2011 | ......... A61F 9/00808 |
| JP | 2011-205345 | 10/2011 | |
| JP | 2011233161 A | 11/2011 | |
| JP | 2012053623 | 3/2012 | |
| JP | 2013-505782 | 2/2013 | |
| JP | 2013-534154 | 9/2013 | |
| JP | 5715316 B1 | 5/2015 | |
| JP | 2018122118 A | 8/2018 | |
| WO | WO 94/08315 | 4/1994 | |
| WO | WO 95/26682 | 10/1995 | |
| WO | WO 96/38815 | 12/1996 | |
| WO | WO 96/41567 | 12/1996 | |
| WO | WO 97/17894 | 5/1997 | |
| WO | WO 97/49065 | 12/1997 | |
| WO | WO 98/11524 | 3/1998 | |
| WO | WO 98/32371 | 7/1998 | |
| WO | WO 98/43201 | 10/1998 | |
| WO | WO 99/38433 | 8/1999 | |
| WO | WO 99/42977 | 8/1999 | |
| WO | WO 99/63887 | 12/1999 | |
| WO | WO 00/07501 | 2/2000 | |
| WO | WO 00/32106 | 6/2000 | |
| WO | WO-2000/041626 | 7/2000 | |
| WO | WO 00/55812 | 9/2000 | |
| WO | WO 00/55814 | 9/2000 | |
| WO | WO 00/68749 | 11/2000 | |
| WO | WO 00/72272 | 11/2000 | |
| WO | WO 01/22362 | 3/2001 | |
| WO | WO 01/85030 | 11/2001 | |
| WO | WO 02/29764 | 4/2002 | |
| WO | WO 02/095686 | 11/2002 | |
| WO | WO 03/034336 | 4/2003 | |
| WO | WO 03/060553 | 7/2003 | |
| WO | WO 03/081529 | 10/2003 | |
| WO | WO 2004/010374 | 1/2004 | |
| WO | WO 2004/012152 | 2/2004 | |
| WO | WO 2004/066807 | 8/2004 | |
| WO | WO 2004/068406 | 8/2004 | |
| WO | WO 2004/072903 | 8/2004 | |
| WO | WO 2005/004038 | 1/2005 | |
| WO | WO 2005/004721 | 1/2005 | |
| WO | WO 2005/027765 | 3/2005 | |
| WO | WO 2005/031635 | 4/2005 | |
| WO | WO 2005/083633 | 9/2005 | |
| WO | WO 2005/119578 | 12/2005 | |
| WO | WO 2006/020920 | 2/2006 | |
| WO | WO 2006/061815 | 6/2006 | |
| WO | WO 2006/066122 | 6/2006 | |
| WO | WO 2006061814 A1 * | 6/2006 | ............ A61B 6/507 |
| WO | WO 2006/079042 | 7/2006 | |
| WO | WO 2006076409 | 7/2006 | |
| WO | WO 2006/082558 | 8/2006 | |
| WO | WO 2007/020555 | 2/2007 | |
| WO | WO-2007/059172 | 5/2007 | |
| WO | WO 2007/066249 | 6/2007 | |
| WO | WO 2007/102858 | 9/2007 | |
| WO | WO 2006/002353 | 1/2008 | |
| WO | WO 2008/030192 | 3/2008 | |
| WO | WO 2009/007910 | 1/2009 | |
| WO | WO 2009/056147 | 5/2009 | |
| WO | WO 2011/038044 | 3/2011 | |
| WO | WO 2012/021307 | 2/2016 | |

OTHER PUBLICATIONS

European Search Report in EP Patent Application No. EP 12 171 882.9 dated Oct. 8, 2012, 3 pages.
U.S. Appl. No. 61/210,401 to Charles A. Taylor et al. titled "Patient-Specific Hemodynamics of the Cardiovascular System," filed Mar. 17, 2009.
Ellwein, Laura M. et al., "Sensitivity Analysis and Model Assessment: Mathematical Models for Arterial Blood Flow and Blood Pressure," Cardiovasc Eng. Jun. 2008; 8(2):94-108.
Spilker, Ryan L. et al., "Morphometry-Based Impedance Boundary Conditions for Patient-Specific Modeling of Blood Flow in Pulmonary Arteries," Annals of Biomedical Engineering, 2007, 35:546-559.
Santamarina, Aland et al., "Computational Analysis of Flow in a Curved Tube Model of the Coronary Arteries: Effects of Time-Varying Curvature," Annals of Biomedical Engineering, 1998, 26:944-954.
Boutsianis, Evangelos et al., "Computational Simulation of Intracoronary Flow Based on Real Coronary Geometry," European Journal of Cardio-thoracic Surgery, 2004, 26:248-256.
Quarteroni, Alfio et al., "Coupling Between Lumped and Distributed Models for Blood Flow Problems," Comput Visual Sci, 2001, 4:111-124.
Berry, Joel L. et al., "Experimental and Computational Flow Evaluation of Coronary Stents," Annals of Biomedical Engineering, 2000, 28:386-398.
Myers, J.G. et al., "Factors Influencing Blood Flow Patterns in the Human Right Coronary Artery," Annals of Biomedical Engineering, 2001, 29:109-120.
Lagana, Katia et al., "Multiscale Modeling of the Cardiovascular System: Application to the Study of Pulmonary and Coronary Perfusions in the Univentricular Circulation, "Journal of Biomechanics, 2005, 38:1129-1141.
Qiu, Yuchen et al., "Numerical Simulation of Pulsatile Flow in a Compliant Curved Tube Model of a Coronary Artery," Journal of Biomechanical Engineering, 2000, 122:77-85.
Formaggia, L. et al., "Numerical Treatment of Defective Boundary Conditions for the Navier-Stokes Equations," SIAM J. Numer. Anal. 2002, 40(1):376-401.
Gijsen, Frank J.H. et al., "Strain Distribution Over Plaques in Human Coronary Arteries Relates to Shear Stress," Am. J. Physiol. Heart Circ. Physiol, 2008, 295:H1608-H1614.
Perktold, K. et al., "Validated Computation of Physiologic Flow in a Realistic Coronary Artery Branch," Journal of Biomechanics, 1998, 31:217-228.
Taylor, Charles A. et al., "Open Problems in Computational Vascular Biomechanics: Hemodynamics and Arterial Wall Mechanics," Comput. Methods Appl. Mechn. Engrg., 2009, 198:3514-3523.
Taylor, Charles A. et al., "Patient-Specific Modeling of Cardiovascular Mechanics," Annu. Rev. Biomed. Eng., 2009, 11:109-134.
Taylor, Charles A. et al., "Image-Based Modeling of Blood Flow and Vessel Wall Dynamics: Applications, Methods and Future Directions," Annals of Biomedical Engineering, Mar. 2010, vol. 38, No. 3, pp. 1188-1203.
Spilker, Ryan L. et al., "Tuning Multidomain Hemodynamic Simulations to Match Physiological Measurements," Annals of Biomedical Engineering, Aug. 2010, vol. 38, No. 8, pp. 2635-2648.
Spilker, Ryan L. et al., "Models and Methods in Computational Vascular and Cardiovascular Mechanics," $9^{th}$ U.S. National Congress on Computational Mechanics, 2007, 1 page.
Spilker, Ryan L. et al., "Tuning Hemodynamics Simulations with Three-Element Windkessel Outlet Boundary Conditions," Jul. 24, 2007, 32 pages.
Taylor, Charles A., "The HeartFlow Concept Combining Angiographic Imaging and Non-invasive Hemodynamic Lesion Assessment: Technology Description," Transcatheter Cardiovascular Therapeutics (TCT) Conference 2010, Sep. 21, 2010, 12 pages.
Erglis, Andrejs et al., "Non-invasive FFR Using Coronary CT Angiography and Computational Fluid Dynamics Predicts the Hemodynamic Significance of Coronary Lesions, " Aug. 29, 2010, 19 pages.

(56) References Cited

OTHER PUBLICATIONS

Taylor, Charles A. et al., "Predictive Medicine: Computational Techniques in Therapeutic Decision-Making," Computer Aided Surgery, 1999, 4:231-247.
Taylor, Charles A. et al., "Computational Investigations in Vascular Disease," Computers in Physics, vol. 10, No. 3, May/Jun. 1996, pp. 224-232.
Taylor, Charles A., "A Computational Framework for Investigating Hemodynamic Factors in Vascular Adaptation and Disease," Aug. 1996, 118 pages.
Wang, Kenneth C., "Improving Geometric Model Construction for Blood Flow Modeling," IEEE Engineering in Medicine and Biology, Nov./Dec. 1999, pp. 33-39.
Pijls, N. et al., "Measurement of Fractional Flow Reserve to Assess the Functional Severity of Coronary-Artery Stenoses," The New England Journal of Medicine, Jun. 27, 1996, pp. 1703-1708, vol. 334, No. 26.
Kim, H.J. et al., "Patient-Specific Modeling of Blood Flow and Pressure in Human Coronary Arteries," Annals of Biomedical Engineering, pp. 3195-3209, vol. 38, No. 10, Oct. 2010.
Kim, H.J. et al., "Coronary Outflow Boundary Condition Coupling Lumped Parameter Coronary Vascular Bed and Heart Models for Three-Dimensional Simulations of Blood Flow," Presented at the Fifth International Biofluids Symposium and Workshop, Pasadena, CA, Mar. 28-30, 2008.
Fischer, A. et al., "Predicting plaque rupture: enhancing diagnosis and clinical decision-making in coronary artery diseases," Vascular Medicine 2000, 5:163-172.
Malek, A.M. et al., "Hemodynamic Shear Stress and its Role in Atherosclerosis," JAMA, Dec. 1, 1999, vol. 282, No. 21, pp. 2035-2042.
Bekkers, E.J. et al., "Multiscale Vascular Surface Model Generation from Medical Imaging Data Using Hierarchical Features," IEEE Transactions on Medical Imaging, vol. 27, No. 3, Mar. 2008, pp. 331-341.
Ku, J.P. et al., "In Vivo Validation of Numerical Prediction of Blood Flow in Arterial Bypass Grafts," Annals of Biomedical Engineering, vol. 30, pp. 743-752, 2002.
Xiong, Guanglei et al., "Virtual Interventions for Image-Based Blood Flow Computation," Computer-Aided Design, vol. 44, No. 1, Jan. 31, 2012, pp. 3-14.
James E. Moore Jr., et al., "Coronary artery bifurcation biomechanics and implications for interventional strategies", Catheterization and Cardiovascular interventions, Nov. 15, 2010, vol. 76, Issue 6, p. 836-843.
Yow, Kin Choong et al.; "Mobile commerce applications; Chapter 3—Jave 2 Micro Edition for Wireless Enterprise Applications"; Jan. 1, 2004; pp. 1-3.
Colombo, Antonio, et al; "Selection of Coronary Stents"; Journal of the American College of Cardiology, vol. 40, No. 6, Sep. 21, 2002, pp. 1021-1033.
European Search Report released in EP Application No. EP 17 17 7516 (publication No. EP 3 258 446 A1); dated Oct. 6, 2017 (3 pages); Annex (4 pages).
Angioplasty—Wikipedia, the free encyclopedia; Feb. 2011; 6 pp. (https://en.wikipedia.org/w/index.php?title=Angioplasty&oldid=414640562).
Appanaboyina, Sunil, et al. "Simulation of intracranial aneurysm stenting: techniques and challenges." Computer Methods in Applied Mechanics and Engineering 198.45-46 (2009): 3567-3582.
Kessler: Cardioweb; 3 pp.; 2006 (www.shodor.org/master/biomed/physio/cardioweb/application.html).
Tsang, J. S., et al. "Virtual reality simulation in endovascular surgical training." The Surgeon 6.4 (2008): 214-220.

\* cited by examiner

METHOD AND SYSTEM FOR PROVIDING INFORMATION FROM A PATIENT-SPECIFIC MODEL OF BLOOD FLOW

RELATED APPLICATIONS

This application is a continuation of U.S. patent application Ser. No. 15/268,031, filed Sep. 16, 2016, which is a continuation of U.S. patent application Ser. No. 14/177,630 (now U.S. Pat. No. 9,517,040), filed Feb. 11, 2014, which is a continuation of U.S. patent application Ser. No. 14/030,801 (now U.S. Pat. No. 8,706,457), filed Sep. 18, 2013, which is a continuation of U.S. patent application Ser. No. 13/470,802 (now U.S. Pat. No. 8,548,778), filed May 14, 2012, the entirety of each of which is incorporated herein by reference.

FIELD

Embodiments include methods and systems for using models of fluid flow and more particularly methods and systems for providing information from patient-specific models of blood flow.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers). These noninvasive tests, however, do not predict outcomes of interventions.

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA cannot provide direct information on the functional significance of coronary lesions, e.g., whether the lesions affect blood flow. In addition, since CCTA is purely a diagnostic test, it does not predict outcomes of interventions.

Invasive testing may also be performed on patients. For example, diagnostic cardiac catheterization may include performing conventional coronary angiography (CCA) to gather anatomic data on coronary lesions by providing a doctor with an image of the size and shape of the arteries. However, CCA also does not predict outcomes of interventions.

Thus, a need exists for a method to predict outcomes of medical, interventional, and surgical treatments on coronary artery blood flow.

It is to be understood that both the foregoing general description and the following detailed description are exemplary and explanatory only and are not restrictive of the disclosure.

SUMMARY

In accordance with an embodiment, a system for providing blood flow information for a patient may include at least one computer system including a touchscreen. The at least one computer system may be configured to display, on the touchscreen, a three-dimensional model representing at least a portion of an anatomical structure of the patient based on patient-specific data. The at least one computer system may also be configured to receive a first input relating to a first location on the touchscreen indicated by at least one pointing object controlled by a user, and the first location on the touchscreen may indicate a first location on the displayed three-dimensional model. The at least one computer system may be further configured to display first information on the touchscreen, and the first information may indicate a blood flow characteristic at the first location.

In accordance with another embodiment, a method for providing patient-specific blood flow information using at least one computer system including a touchscreen may include displaying, on the touchscreen, a three-dimensional model based on patient-specific data. The three-dimensional model may represent at least a portion of an anatomical structure of the patient. The method may also include receiving a first input relating to a first location on the touchscreen indicated by at least one pointing object controlled by a user, and the first location on the touchscreen may indicate a first location in the displayed three-dimensional model. The method may also include displaying first information on the touchscreen, and the first information may indicate a blood flow characteristic at the location in the three-dimensional model indicated by the first input. The method may further include receiving a second input indicating a modification of the three-dimensional model and determining second information regarding the blood flow characteristic in the anatomical structure based on the modification of the three-dimensional model.

In accordance with a further embodiment, a non-transitory computer readable medium for use on at least one computer system may contain computer-executable programming instructions for performing a method for providing patient-specific blood flow information. The at least one computer system may include a touchscreen, and the method may include displaying a three-dimensional model representing at least a portion of an anatomical structure of the patient based on patient-specific data and receiving a first input relating to a first location on the touchscreen indicated by at least one pointing object controlled by a user. The first input may indicate a location of a stent for placement in the anatomical structure. The method may also include displaying the stent on the three-dimensional model on the touchscreen and determining second information regarding a blood flow characteristic at a plurality of locations in the three-dimensional model based on a modification of the three-dimensional model reflecting the placement of the stent at the location indicated in the first input.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

In an exemplary embodiment, a method and system determines various information relating to blood flow in a specific patient using information retrieved from the patient. The determined information may relate to blood flow in the patient's coronary vasculature. Alternatively, the determined information may relate to blood flow in other areas of the patient's vasculature, such as carotid, peripheral, abdominal, renal, and cerebral vasculature.

The coronary vasculature includes a complex network of vessels ranging from large arteries to arterioles, capillaries, venules, veins, etc. The coronary vasculature circulates blood to and within the heart and includes an aorta 2 (FIG. 2) that supplies blood to a plurality of main coronary arteries 4 (FIG. 2) (e.g., the left anterior descending (LAD) artery, the left circumflex (LCX) artery, the right coronary (RCA) artery, etc.), which may further divide into branches of arteries or other types of vessels downstream from the aorta 2 and the main coronary arteries 4. Thus, the exemplary method and system may determine various information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure gradient, pressure (or a ratio thereof), flow rate, and fractional flow reserve (FFR) at various locations in the aorta, the main coronary arteries, and/or other coronary arteries or vessels downstream from the main coronary arteries. This information may be used to determine whether a lesion is functionally significant and/or whether to treat the lesion, and/or to predict the results of various treatment options. This information may be determined using information obtained noninvasively from the patient. As a result, the decision whether to treat a lesion may be made without the cost and risk associated with invasive procedures.

Figure 1:
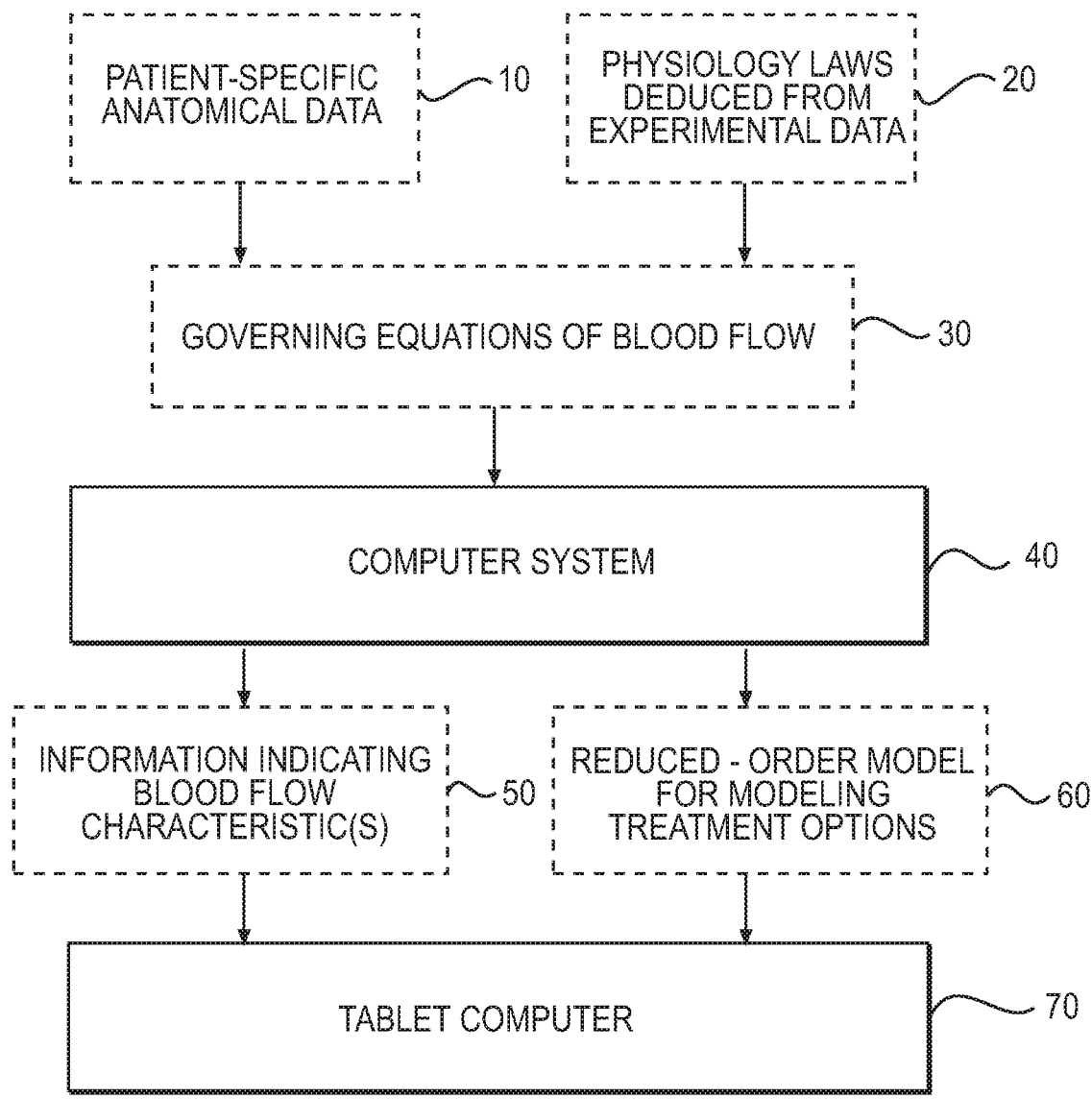
FIG. 1 is a schematic diagram of a system for providing various information relating to blood flow in a specific patient, according to an embodiment.

FIG. 1 shows aspects of a system for providing various information relating to coronary blood flow in a specific patient, according to an embodiment. Additional details relating to various embodiments of methods and systems for determining blood flow information in a specific patient are disclosed, for example, in U.S. Patent Application Publication No. 2012/0041739 entitled "Method And System For Patient-Specific Modeling Of Blood Flow," which is incorporated by reference in its entirety.

Patient-specific anatomical data 10 may be obtained, such as data regarding the geometry of the patient's heart, e.g., at least a portion of the patient's aorta, a proximal portion of the main coronary arteries (and the branches extending therefrom) connected to the aorta, and the myocardium. The patient-specific anatomical data 10 may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The resulting imaging data (e.g., provided by CCTA, MRI, etc.) may be provided by a third-party vendor, such as a radiology lab or a cardiologist, by the patient's physician, etc. Other patient-specific anatomical data 10 may also be determined from the patient noninvasively, e.g., blood pressure in the patient's brachial artery (e.g., using a pressure cuff), such as the maximum (systolic) and minimum (diastolic) pressures.

A three-dimensional model 12 (FIGS. 2 and 3) of the patient's anatomy may be created using the patient-specific anatomical data 10. In an embodiment, the portion of the patient's anatomy that is represented by the model 12 may include at least a portion of the aorta 2 and a proximal portion of the main coronary arteries 4 (and the branches extending or emanating therefrom) connected to the aorta 2. The three-dimensional model 12 may also include other portions of the patient's anatomy, such as the left and/or right ventricles, calcium and/or plaque within the coronary arteries 4 and/or the branches, other tissue connected to and/or surrounding the coronary arteries 4 and/or the branches, etc.

Various physiological laws or relationships 20 relating to coronary blood flow may be deduced, e.g., from experimental data. Using the model 12 and the deduced physiological laws 20, a plurality of equations 30 relating to coronary blood flow may be determined. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, pressure gradients, FFR, etc.) relating to the coronary blood flow in the patient's anatomy at various points in the anatomy represented by the model 12.

In an embodiment, the model 12 may be prepared for analysis and boundary conditions may be determined. For example, the model 12 may be trimmed and discretized into a volumetric mesh, e.g., a finite element or finite volume mesh. The volumetric mesh may be used to generate the equations 30.

Boundary conditions may be determined using the physiological laws 20 and incorporated into the equations 30. The boundary conditions may provide information about the model 12 at its boundaries, e.g., the inflow boundaries, the outflow boundaries, the vessel wall boundaries, etc. The inflow boundaries may include the boundaries through which flow is directed into the anatomy of the three-dimensional model, such as at an end of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an end of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the model 12.

The equations 30 may be solved using a computer system 40. Based on the solved equations 30, the computer system 40 may output information 50 indicating one or more blood flow characteristics, such as FFR, blood pressure (or pressure gradient), blood flow, or blood velocity, determined based on the solution of the equations 30. The computer system 40 may output images generated based on the model 12 and the information 50 or other results of the computational analysis, as described below. The information 50 may be determined under simulated conditions of increased coronary blood flow or hyperemia conditions, e.g., conventionally induced by intravenous administration of adenosine. For example, the boundary conditions described above may specifically model conditions of increased coronary blood flow, hyperemia conditions, and/or the effect of adenosine.

Figure 2:
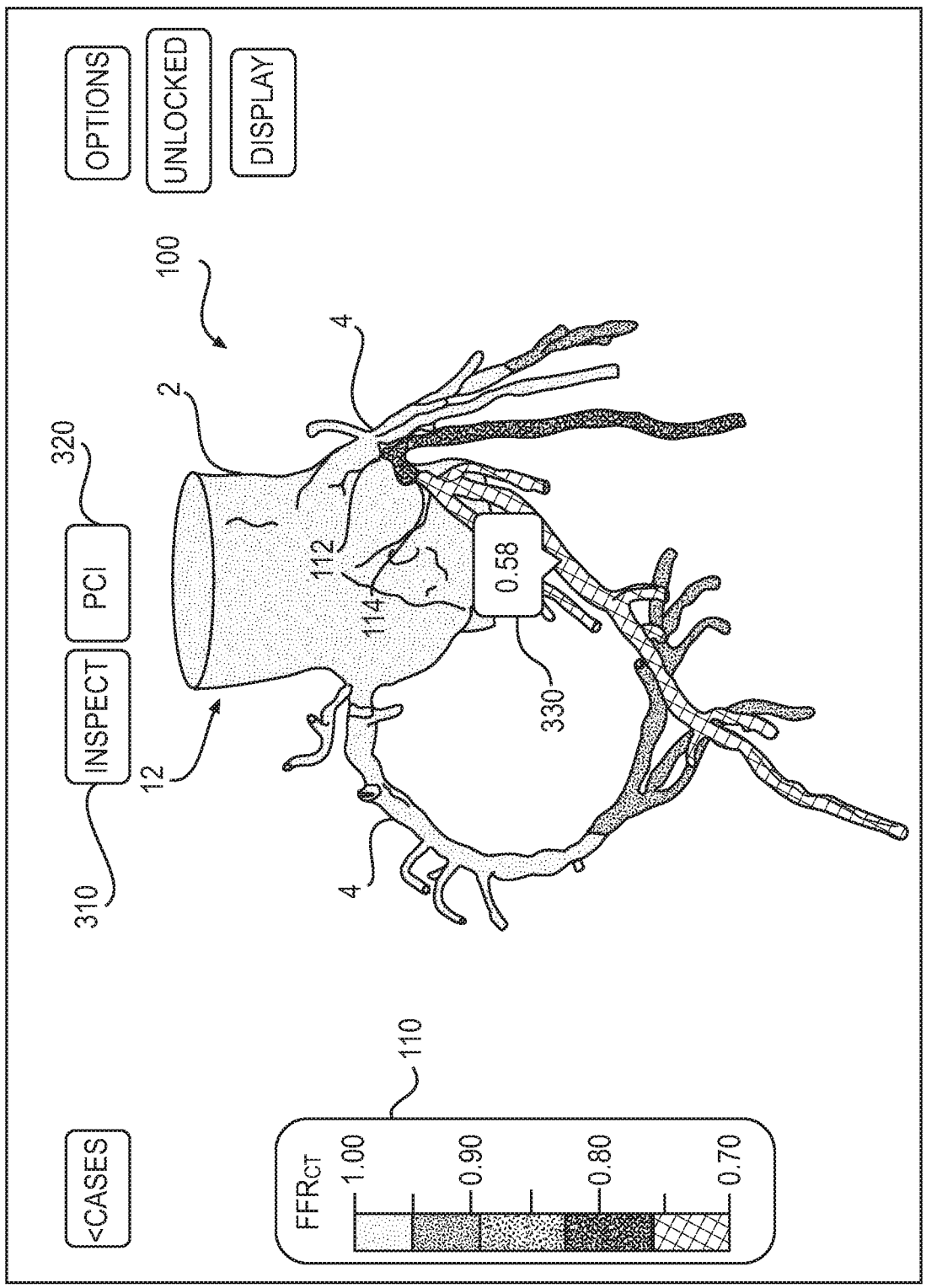
FIG. 2 is an image showing calculated fractional flow reserve (FFR) within a three-dimensional model representing a portion of a patient's aorta and a plurality of coronary arteries emanating from the patient's aorta, according to an embodiment.

FIG. 2 shows a computed FFR model 100 that may be output from the computer system 40. The computed FFR model 100 may include the geometry of the anatomical structure based on the model 12 and may also indicate the information 50 output from the computer system 40, such as the values of FFR at various locations along three-dimensions in the model 12. FFR may be calculated as the ratio of the blood pressure at a particular location in the model 12 (e.g., in a coronary artery) divided by the blood pressure in the aorta, e.g., at the inflow boundary of the model 12, under conditions of increased coronary blood flow or hyperemia conditions. A corresponding color, shade, pattern, or other visual indicator may be assigned to the respective FFR values throughout the computed FFR model 100 such that the computed FFR model 100 may visually indicate the variations in FFR throughout the model 100 without having to visually indicate the individual numerical values for each point in the model 100.

A scale or key 110 may be provided that indicates which numerical values of FFR correspond to which colors, shades, patterns, or other visual indicators. For example, the computed FFR model 100 may be provided in color, and a color spectrum may be used to indicate variations in computed FFR throughout the model 100. The color spectrum may include red, yellow, green, cyan, and blue, in order from lowest computed FFR (indicating functionally significant lesions) to highest computed FFR. For example, the upper limit (blue) may indicate an FFR of 1.0, and the lower limit (red) may indicate approximately 0.7 (or 0.75 or 0.8) or less, with green indicating approximately 0.85 (or other value approximately halfway between the upper and lower limits). For example, the lower limit may be determined based on a lower limit (e.g., 0.7, 0.75, or 0.8) used for determining whether the computed FFR indicates a functionally significant lesion or other feature that may require intervention. Thus, the computed FFR model 100 for some patients may show a majority or all of the aorta as blue or other color towards the higher end of the spectrum, and the colors may change gradually through the spectrum (e.g., towards the lower end of the spectrum (down to anywhere from red to blue)) towards the distal ends of the coronary arteries and the branches that extend therefrom. The distal ends of the coronary arteries for a particular patient may have different colors, e.g., anywhere from red to blue, depending on the local values of computed FFR determined for the respective distal ends.

For example, the computed FFR model 100 of FIG. 2 may show that, for this particular patient, under simulated hyperemia conditions, the computed FFR is generally uniform and approximately 1.0 in the aorta (e.g., as indicated by the color blue), and that the computed FFR gradually and continuously decreases (e.g., to values ranging from near 1.0 down to approximately 0.9, as indicated by gradually changing colors from blue to cyan or a mix of blue and cyan) as the blood flows downstream into the main coronary arteries and into the branches. However, at certain areas, such as areas 112 and 114, there may be sharper decreases in computed FFR. For example, between the aorta and area 112 in one of the coronary arteries, the computed FFR model 100 may indicate generally constant values (e.g., approximately 1.0, as indicated by the color blue) or gradually decreasing values in computed FFR (e.g., to values ranging from near 1.0 down to approximately 0.9, as indicated by gradually changing colors from blue to cyan or a mix of blue and cyan). At area 112, the computed FFR model 100 may indicate a drop in computed FFR to approximately 0.8 (e.g., as indicated by colors changing from blue and/or cyan, to green and/or yellow). Between the areas 112 and 114, the computed FFR model 100 may indicate generally constant values (e.g., approximately 0.8, as indicated by the colors green and/or yellow) or gradually decreasing values in computed FFR (e.g., to values slightly less than 0.8, as indicated by colors that are more yellow than green). At area 114, the computed FFR model 100 may indicate a drop in computed FFR to approximately 0.7 or below (e.g., as indicated by colors changing from green and/or yellow, to red). Downstream of the area 114 and to the distal end of the coronary artery, the computed FFR model 100 may indicate that the computed FFR is approximately 0.7 or below (e.g., as indicated by the color red).

Based on the computed FFR model 100, a user may determine that the computed FFR has dropped below the lower limit used for determining the presence of a functionally significant lesion or other feature that may require intervention (e.g., based on the location(s) of areas colored red in the computed FFR model 100 or otherwise indicating a value of computed FFR that is below the lower limit), and the user may also be able to locate the functionally significant lesion(s). The user may locate the functionally significant lesion(s) based on the geometry of the artery or branch (e.g., using the computed FFR model 100). For example, the functionally significant lesion(s) may be located by finding a narrowing or stenosis located near (e.g., upstream from) the location(s) of the computed FFR model 100 indicating the local minimum FFR value.

Figure 3:
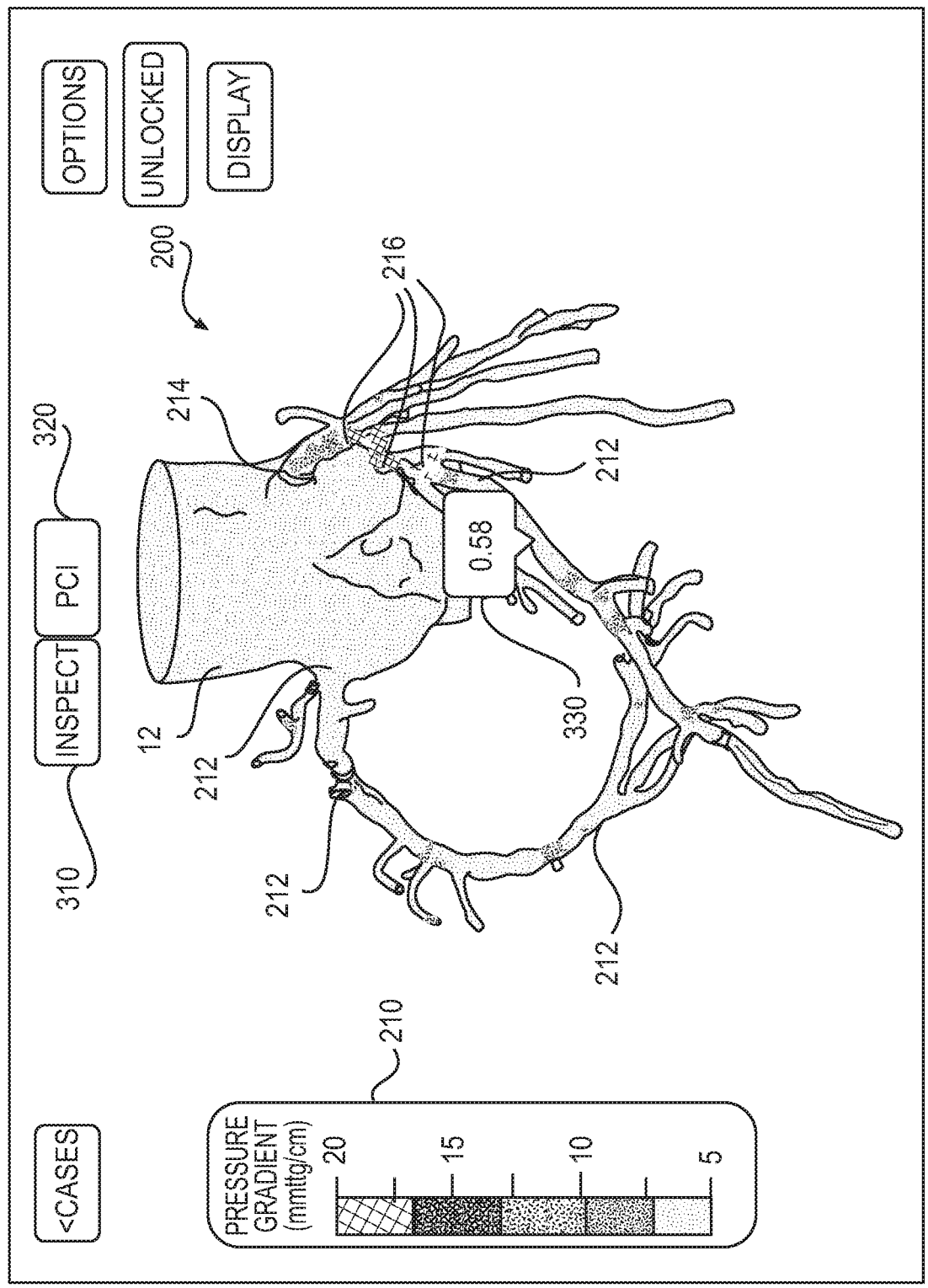
FIG. 3 is an image showing calculated pressure gradient within a three-dimensional model representing a portion of a patient's aorta and a plurality of coronary arteries emanating from the patient's aorta, according to an embodiment.

FIG. 3 shows a computed pressure gradient model 200 that may be output from the computer system 40. The computed pressure gradient model 200 may include the geometry of the anatomical structure based on the model 12 and may also indicate the information 50 output from the computer system 40, such as the values of blood pressure gradient at various locations along three-dimensions in the model 12. The computed pressure gradient model 200 may show the local blood pressure gradient (e.g., in millimeters of mercury (mmHg) per centimeter) throughout the model 12 under simulated hyperemia conditions or other conditions. A corresponding color, shade, pattern, or other visual indicator may be assigned to the respective pressures gradients such that the model 200 may visually indicate variations in pressure gradient throughout the model 200 without having to visually indicate the individual pressure gradient numerical values for each point in the model 200.

A scale or key 210 may be provided that indicates which numerical values of pressure gradient correspond to which colors, shades, patterns, or other visual indicators. For example, the computed pressure gradient model 200 may be provided in color, and a color spectrum may be used to indicate variations in pressure throughout the model 200. The color spectrum may include red, yellow, green, cyan, and blue, in order from highest pressure gradient, which may indicate functionally significant lesions, to lowest pressure gradient. For example, the upper limit (red) may indicate approximately 20 mmHg/cm or more, and the lower limit (blue) may indicate approximately 0 mmHg/cm or less, with green indicating approximately 10 mmHg/cm (or other value approximately halfway between the upper and lower limits). Thus, the computed pressure gradient model 200 for some patients may show a majority or all of the aorta as blue and/or cyan, or other color towards the lower end of the spectrum, and the colors may change gradually through the spectrum (e.g., towards the higher end of the spectrum (up to red)) at areas having higher pressure gradients.

For example, the computed pressure gradient model 200 of FIG. 3 may show that, for this particular patient, under simulated hyperemia conditions, the pressure gradient may be generally uniform and approximately zero mmHg/cm (e.g., as indicated by the colors blue and/or cyan) in the aorta and in most of the main coronary arteries and the branches. The computed pressure gradient model 200 may indicate a gradual increase in pressure gradient such that some areas 212 in the main coronary arteries and the branches indicate values of approximately 5 mmHg/cm to approximately 10 mmHg/cm (e.g., as indicated by the colors cyan and/or green), some areas 214 in the main coronary arteries and the branches indicate values of approximately 10 mmHg/cm to approximately 15 mmHg/cm (e.g., as indicated by the colors green and/or yellow), and some areas 216 in the main coronary arteries and the branches indicate values of greater than approximately 15 mmHg/cm (e.g., as indicated by the colors yellow and/or red).

Based on the computed pressure gradient model 200, a user may determine that the computed pressure gradient has increased above a certain level (e.g., approximately 20 mmHg/cm), which may indicate the presence of a functionally significant lesion or other feature that may require intervention, and the user may also be able to locate the functionally significant lesion(s). The user may locate the functionally significant lesion(s) based on the geometry of the artery or branch (e.g., using the computed pressure gradient model 200). For example, the functionally significant lesion(s) may be located by finding a narrowing or stenosis located near the location(s) of the computed pressure gradient model 200 indicating a value of approximately 20 mmHg/cm or higher.

The computer FFR model 100, the computed blood pressure gradient model 200, or other model may also include other information, such as geometry information (e.g., numerical values for vessel inner diameter, thickness, etc.), throughout the model 100 or 200. The information relating to a particular location on the model may be displayed to the user upon selection of the location of the model as described below.

The computer system 40 may allow the user to select whether to output the computed FFR model 100, the computed blood pressure gradient model 200, or other model, and/or to specify other color mappings or rendering styles (e.g., x-ray rendering).

Referring back to FIG. 1, the computer system 40 may include one or more non-transitory computer-readable storage devices that store instructions that, when executed by a processor, computer system, etc., may perform any of the actions described herein for providing various information relating to blood flow in the patient. The computer system 40 may include a desktop or portable computer, a workstation, a server, a personal digital assistant, or any other computer system. The computer system 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer system 40 to a network, a display adapter for connecting the computer system 40 to a display, etc. For example, the display may be used to display the model 12 and/or any images generated by solving the equations 30 (e.g., the computed FFR model 100, the computed blood pressure gradient model 200, and/or the other models described below).

The patient-specific anatomical data 10 may be transferred over a secure communication line (e.g., via a wireless or wired network) to the computer system 40, which may create the model 12 and solve the equations 30. For example, in an embodiment, the data 10 may be transferred from the third-party vendor that obtains the patient-specific anatomical data 10 to the computer system 40 operated by the patient's physician or other user.

In an embodiment, the computer system 40 may output the information 50 indicating one or more blood flow characteristics, the computed FFR model 100, the computed blood pressure gradient model 200, and/or other output from the computer system 40 based on the solution of the equations 30 to a tablet computer 70 (or other mobile or handheld computing device), such as Apple Inc.'s iPad®, over a secure communication line (e.g., via a wireless or wired network, using a web-based service, etc.). The tablet computer 70 may be operated by the patient's physician or other user, such as the patient. The tablet computer 70 may include a touchscreen. Various screenshots of the touchscreen are shown in FIGS. 2-6 and described below. The touchscreen may be configured to receive input from the user based on contact by at least one of the user's digits (e.g., at least one of the user's fingers or thumbs) on a surface of the touchscreen as described below. The following description relates to embodiments in which the touchscreen is configured to receive input from contact by the user's finger(s) on the surface of the touchscreen. However, it is understood that the touchscreen may be configured to receive input from the user based on contact or sensed proximity to the touchscreen by the user's finger(s), the user's thumb(s), a stylus, another pointing object or instrument, or a combination thereof.

Thus, in an embodiment, the computer system 40 may perform more complicated operations, such as solving the equations 30, while the tablet computer 70 may be a portable system for displaying the results of the solution of the equations 30 by the computer system 40 and for performing less complicated computations. The tablet computer 70 may allow the patient's physician, the patient, or other user to access information from the model 12, 100, or 200, and manipulate the model 12, 100, or 200 as described below. The tablet computer 70 may also be configured to allow the user to select treatment options using the tablet computer 70. The tablet computer 70 may determine or predict the blood flow characteristic(s) (e.g., FFR, blood pressure (or pressure gradient), etc.) in the patient's anatomical structure based on the selected treatment options as described below.

Figure 4:
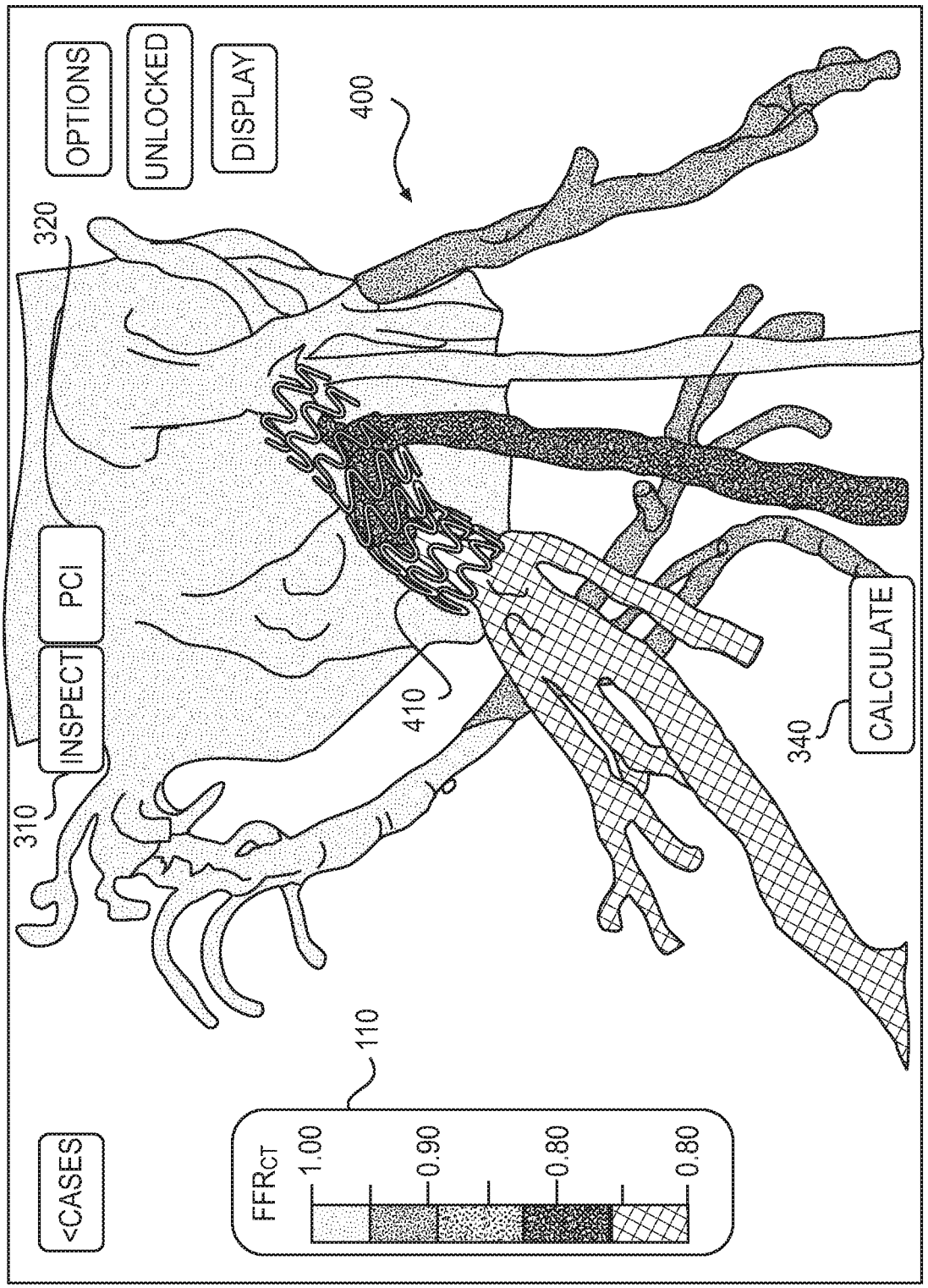
FIG. 4 is an image showing calculated FFR within a three-dimensional model representing a portion of a patient's aorta and a plurality of coronary arteries emanating from the patient's aorta, and a stent for placement in a coronary artery, according to an embodiment.

For example, as shown in FIGS. 2-4, the tablet computer 70 may provide two mode selection buttons 310 and 320 that allow the user to switch between two modes. Touching the first button 310 allows the user to select the first operating mode (e.g., an inspection mode), and touching the second button 320 allows the user to select the second operating mode (e.g., a percutaneous coronary intervention (PCI) mode).

FIGS. 2 and 3 are images illustrating screen shots of the tablet computer 70 operating in the first operating mode. In the first operating mode, the tablet computer 70 may display information indicating one or more blood flow characteristics of the patient in the patient's current condition, e.g., the computed FFR model 100 (FIG. 2), the computed pressure gradient model 200 (FIG. 3), or other model providing the information 50 output from the computer system 40. Inputs received from the user using the tablet computer 70 in the first operating mode may allow the user to interact with and manipulate the displayed information regarding the patient's current condition.

The tablet computer 70 may be configured to determine when the user's finger(s) contact the surface of the touchscreen at a location corresponding to a location on the displayed model 100 or 200 (and a corresponding location in the patient's anatomical structure). Based on this input, the tablet computer 70 may determine the numerical value of a blood flow characteristic (e.g., FFR, blood pressure (or pressure gradient), and/or other blood flow characteristic selected by the user) at the indicated location on the displayed model 100 or 200, and may display the determined numerical value. The displayed numerical value may be dynamically updated as the user drags the finger(s) along the surface of the touchscreen and along the displayed model 100 or 200. Thus, the user may touch any point on the model 12, 100, or 200 to determine the numerical value of any of the blood flow characteristics described above, e.g., FFR, blood pressure (or pressure gradient), and/or other blood flow characteristic, at that point. Additional information relating to the indicated point on the model 12, 100, or 200 may also be displayed to the user, such as geometry information (e.g., a numerical value of the vessel inner diameter, etc.).

For example, the tablet computer 70 may be configured to determine when the user's finger(s) contact the surface of the touchscreen for a predetermined time (e.g., a touch and hold) at a location corresponding to a location on the displayed model 100 or 200. Based on this input, the tablet computer 70 may create a tag or pin 330 that points to the indicated location within the displayed model 100 or 200. The user can then drag or move the pin 330 anywhere within the displayed model 100 or 200 to determine the numerical value of a blood flow characteristic at the indicated location on the displayed model 100 or 200 to which the pin 330 has been dragged. The numerical value may be dynamically updated as the pin 330 is dragged. The tablet computer 70 may display the determined numerical value within or near the pin 330. For example, in FIGS. 2 and 3, the pin 330 points to a location in one of the coronary arteries illustrated in the model 100 where the FFR value is 0.58. The pin 330 may also indicate other information regarding the indicated location, such as a dimension (e.g., diameter) of the vessel at the indicated location. The tablet computer 70 may allow the user to create more than one pin 330 to drag separately around the model 100 or 200, and remove the pin(s) 330, as desired.

When the user's finger(s) contact the surface of the touchscreen (e.g., for less than the amount of time associated with creating the pin 330) at a location corresponding to a location on the displayed model 100 or 200, then the tablet computer 70 may determine that the user has selected a particular coronary artery (and/or the branches connected thereto) and may fade (e.g., dim or decrease the brightness of) the other coronary arteries and branches.

Alternatively, or in addition, the selected location may become a new focal point of view for the displayed model 100 or 200, and/or a new local origin for transformations, such as rotation and zoom. This allows the user to focus in on a potential stenosis, and to rotate around or zoom to (or away from) any user-defined point.

The tablet computer 70 may also be configured to determine when the user's finger(s) swipe or drag on the surface of the touchscreen (e.g., at a location away from the pin 330). Based on this input, the tablet computer 70 may rotate the displayed model 100 or 200. The amount and direction of rotation may depend on the distance that the finger(s) travel in contacting the surface of the touchscreen during the swipe and the direction of the swipe along the surface of the touchscreen.

The tablet computer 70 may also be configured to determine when the uses fingers pinch the surface of the touchscreen. If the user's fingers move closer together, the tablet computer 70 may zoom out from the displayed model 100 or 200. If the user's fingers move away from each other, the tablet computer 70 may zoom in on the displayed model 100 or 200. The amount of the zoom may depend on the distance that the finger(s) travel in the pinch along the surface of the touchscreen.

As the user manipulates the view of the displayed model 100 or 200 (e.g., by rotating, zooming in or away, changing the focal point, etc.), the tube angulation or other information for characterizing the direction from which the anatomical structure is being viewed may be displayed to the user and dynamically updated. For example, the information may be provided in the form of left anterior oblique (LAO), right anterior oblique (RAO), caudal (CAUD), and/or cranial (CRAN) angles, e.g., LAO 20° and CRAN 0°, as known in the art.

Figure 5:
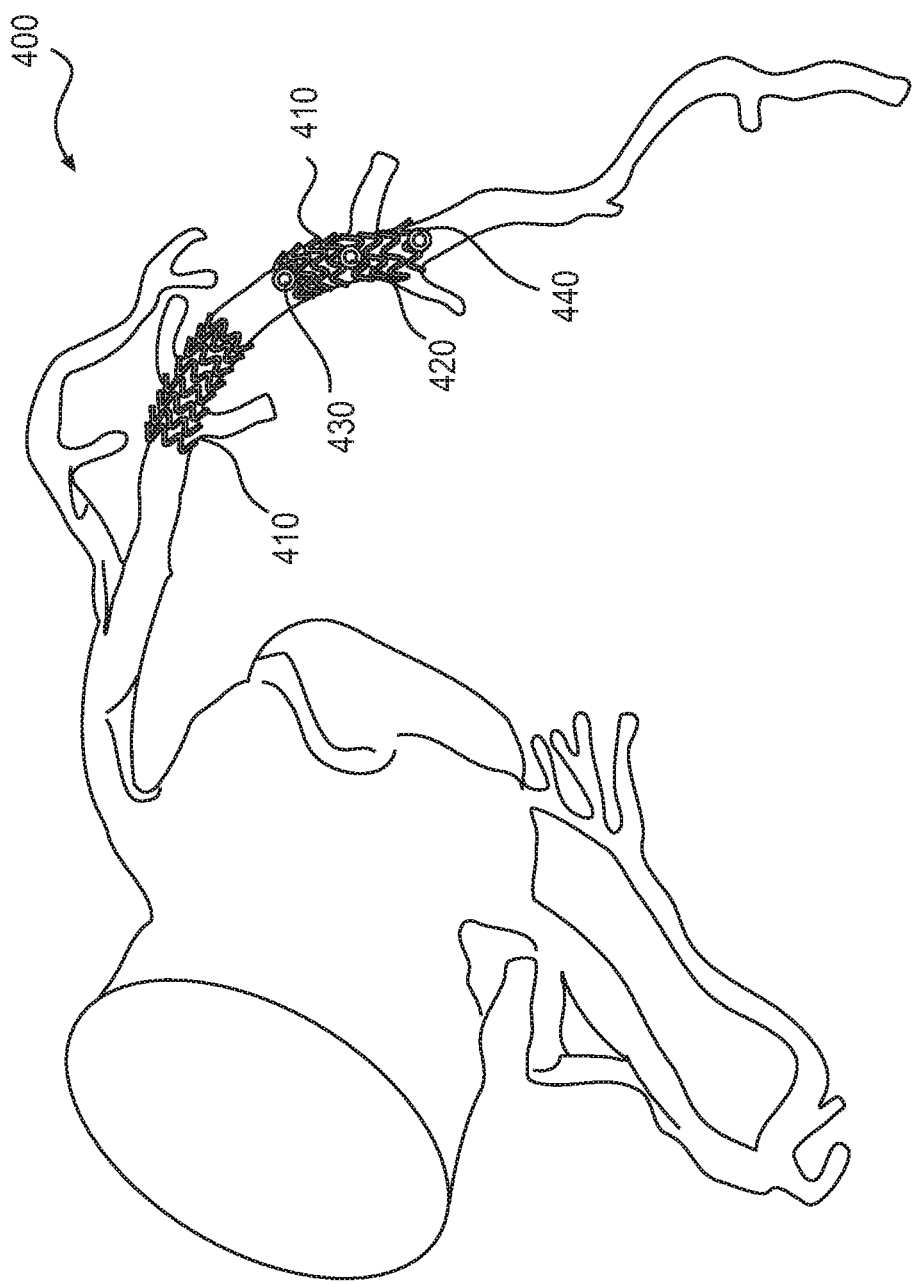
FIG. 5 is an image showing a three-dimensional model representing a portion of a patient's aorta and a plurality of coronary arteries emanating from the patient's aorta, and a plurality of stents for placement in a coronary artery, according to an embodiment.
Figure 6:
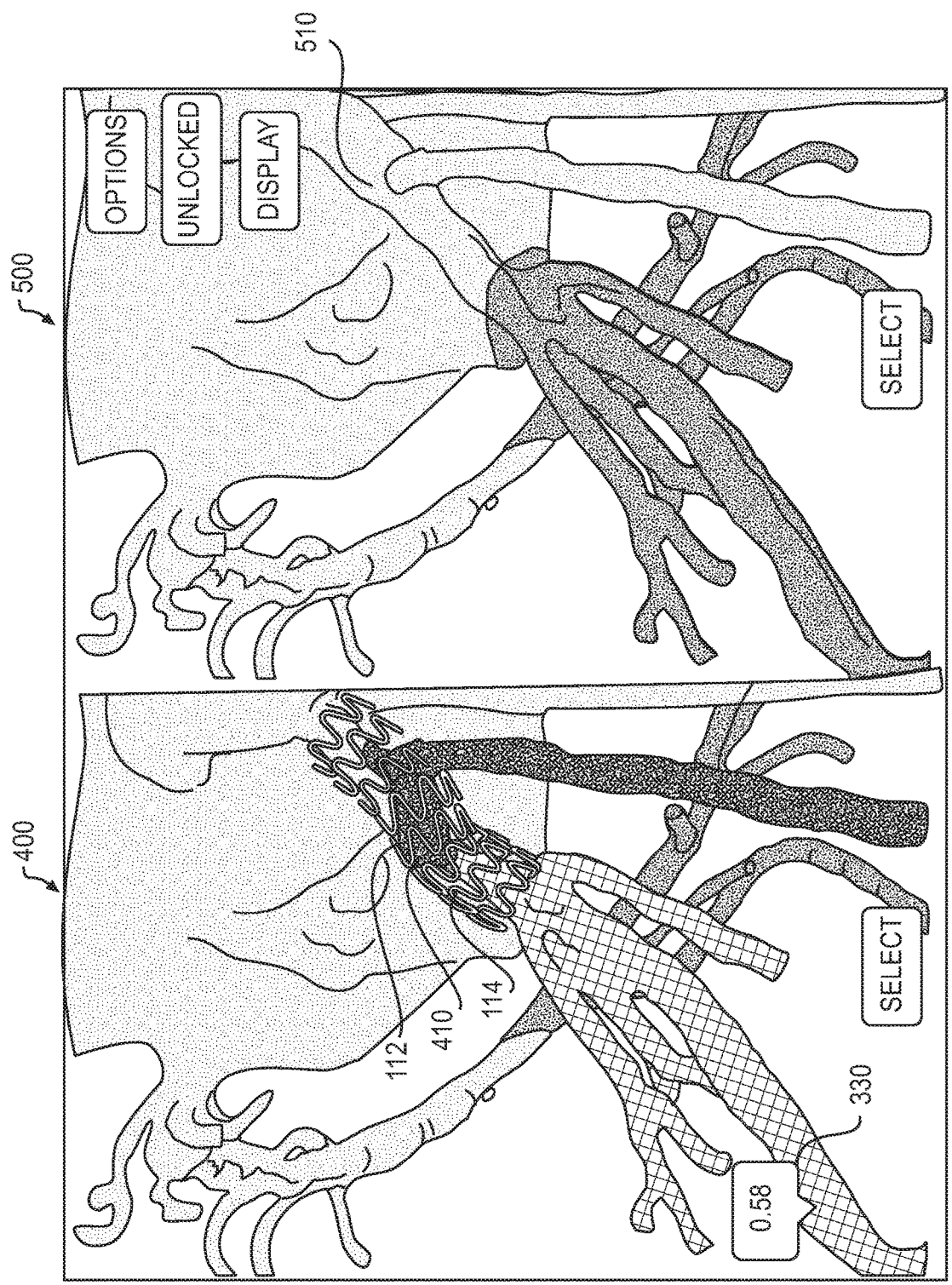
FIG. 6 is an image showing a split screen with the model and stent of FIG. 4 in one screen portion and a three-dimensional model modified based on the placement of the stent in another screen portion, according to an embodiment.

FIGS. 4-6 are images illustrating screen shots of the tablet computer 70 operating in the second operating mode (e.g., the PCI mode) selected by the user by touching the second button 320. Inputs received from the user using the tablet computer 70 in the second operating mode allow the user to plan treatment options using the displayed model 400, which may be created based on the model 12 (e.g., a model reflecting the geometry of the patient's anatomical structure without additional information indicating blood flow characteristic(s)), the computed FFR model 100 (FIG. 2), the computed pressure gradient model 200 (FIG. 3), or other model providing information 50 indicating a blood flow characteristic of the patient in the patient's current condition. The tablet computer 70 may display predicted information regarding the blood flow characteristic(s) (e.g., FFR, blood pressure (or pressure gradient), etc.) based on the selected the treatment option.

FIG. 4 shows a screen shot of the tablet computer 70 operating in the second operating mode to allow the user to select a treatment option using the model 400. In the embodiment shown in FIG. 4, the model 400 is created based on the computed FFR model 100. Alternatively, the model 400 may be created based on the model 12, the computed pressure gradient model 200, and/or other model. The tablet computer 70 may be configured to determine when the user's finger(s) contact the surface of the touchscreen (e.g., for a predetermined time (e.g., a touch and hold)) at a location corresponding to a location on the displayed model 400 (and a corresponding location in the patient's anatomical structure). Based on this input, the tablet computer 70 may display a stent 410 for planned insertion into the patient's anatomical structure (e.g., in a coronary artery). The tablet computer 70 may allow the user to place more than one stent 410 on the model 400, as shown in FIG. 5, and remove the stent(s) 410, as desired.

When initially placed on the model 400, the stent 410 may have a predetermined size or dimension, or other characteristics (e.g., diameter, length, material, wire thickness, wire configuration, etc.). The stent 410 may be initially placed so that the stent 410 is centered longitudinally with respect to the location selected by the user.

The user may then provide additional inputs to define and/or adjust the stent 410. For example, the tablet computer 70 may be configured to determine when the user's finger(s) swipe or drag on the surface of the touchscreen. Based on this input, the tablet computer 70 may move the stent 410 along the model 400. For example, the stent 410 may move parallel to the centerline(s) of the coronary artery or arteries (or branches connected thereto). Also, the shape of the stent 410 may conform to bends and curves in the centerline(s), as shown in FIGS. 4-6, as the stent 410 is dragged or moved along the centerline(s). The amount and direction (e.g., upstream or downstream along the centerline(s)) of movement of the stent 410 may depend on the distance that the finger(s) travel in contacting the surface of the touchscreen during the swipe and the direction of the swipe along the surface of the touchscreen.

The tablet computer 70 may also be configured to determine when the user's fingers pinch the surface of the touchscreen. If the user's fingers move closer together, the tablet computer 70 may shorten the stent 410 (e.g., in the longitudinal direction and/or the direction of the centerline(s)). If the user's fingers move away from each other, the tablet computer 70 may lengthen the stent 410 (e.g., in the longitudinal direction and/or the direction of the centerline(s)). The amount of the change in length may depend on the distance that the finger(s) travel along the surface of the touchscreen to form the pinch. Also, the change in length may be continuous or may be provided in increments (e.g., approximately 4 millimeter increments or other increment). For example, if the stent 410 has a sequential ring configuration (e.g., a series of sequential rings that are joined together to form a tubular structure), then the change in length may be provided in increments that are generally equivalent to a length of one ring, and the touchscreen may show the ring(s) being added or removed from the stent 410 to shorten or lengthen the stent 410.

Other features may be provided that allow the user to adjust and manipulate the stent 410. FIG. 5 shows a screen shot of the tablet computer 70 operating in the second operating mode to allow the user to plan a treatment option associated with the placement of the stent 410 using the model 400, according to another embodiment.

When displaying the stent 410 for planned insertion into the patient's anatomical structure (e.g., in a coronary artery), the tablet computer 70 may create one or more handles, such as a first handle 420, a second handle 430, and/or a third handle 440. The first handle 420 may be located at or near the center of the stent 410 along the longitudinal direction. The user may drag or move the stent 410 along the model 400 by pressing the first handle 420 and dragging the first handle 420 to a desired location on the model 400. Movement of the first handle 420 results in movement of the stent 410. As the user drags the first handle 420 along the model 400, the stent 410 may also move parallel to the centerline(s) of the coronary artery or arteries (or branches connected thereto) until the user removes the finger(s) from the first handle 420. Also, the shape of the stent 410 may conform to bends and curves in the centerline(s) as the stent 410 is dragged or moved along the centerline(s) with the first handle 420.

The second and third handles 430, 440 may be located at or near the proximal and distal ends of the stent 410, respectively. The user may adjust the length of the stent 410 by pressing the second and/or the third handles 430, 440 and dragging the respective second and/or third handles 430, 440 along the model 400, thereby adjusting the locations of the respective proximal and distal ends of the stent 410. Movement of the second and/or third handles 430, 440 results in lengthening/shortening of the stent 410. For example, when the user drags the second handle 430 along the model 400 in a proximal direction away from the third handle 440, the stent 410 may lengthen and extend along the proximal direction. Similarly, when the user drags the third handle 440 along the model 400 in a distal direction away from the second handle 430, the stent 410 may lengthen and extend along the distal direction. The new portion of the stent 410 that is added due to the lengthening may be formed parallel to the centerline(s) of the coronary artery or arteries (or branches connected thereto) and may conform to bends and curves in the centerline(s). Alternatively, the stent 410 may shorten when the user drags the second handle 430 along the model 400 in a distal direction toward the third handle 440 or when the user drags the third handle 440 along the model 400 in a proximal direction toward the second handle 430. As the length of the stent 410 is altered, the placement of the first handle 420 may be automatically adjusted so that the first handle 420 stays at or near the center of the stent 410. As a result, the handles 420, 430, 440 are user-friendly and allow the user to manipulate and adjust the stent 410 as desired.

Various characteristics of the stent 410 may be displayed on the touchscreen. For example, the numerical values of the length, the proximal diameter, and/or the distal diameter of the stent 410 may be displayed on the touchscreen, e.g., in a stent legend. The numerical values may be dynamically updated as the user adjusts the stent 410.

Other characteristics of the stent 410, e.g., the material, wire thickness, wire configuration, etc., may be selected by the user. For example, the tablet computer 70 may provide a selection of stent models that are available for placement into the patient and may store the characteristics of those stent models. The user may select from the stent models, and the tablet computer 70 may retrieve the stored characteristics corresponding to the stent model selected by the user to determine the various characteristics of the stent 410, such as the dimensions of the stent 410. In addition, other characteristics of the stent 410 may be determined based on the stent model selected, such as the dimensions of the incremental changes in length (e.g., the size of the rings in a ring configuration) described above and/or the flexibility of the stent 410 (e.g., the ability to conform to the bends and curves in the centerlines of the coronary arteries and branches).

Alternatively, the various characteristics of the stent 410 and/or the stent model may be determined automatically and recommended by the tablet computer 70 based on various factors, such as the location of any FFR values that are less than 0.75 and the dimensions of the vessels at those locations, locations and dimensions of significant narrowing of the vessels, etc.

The tablet computer 70 may also provide other treatment options for selection by the user, such as other types of surgery on the modeled anatomy that may result in a change in the geometry of the modeled anatomy. For example, the tablet computer 70 may be used to plan a coronary artery bypass grafting procedure. Coronary artery bypass grafting may involve creating new lumens or passageways in the model 400. After selecting this type of treatment option, the tablet computer 70 may be configured to determine when the user's finger(s) contact the surface of the touchscreen (e.g., for a predetermined time (e.g., a touch and hold)) at a location corresponding to a location on the displayed model 400. Based on this first input, the tablet computer 70 may display a bypass segment (not shown) for planned connection to the patient's anatomical structure (e.g., in a coronary artery), which has one end that is connected to the model 400 at the location indicated by the first input. The tablet computer 70 may then prompt the user to provide a second input identifying a second location for connecting the opposite end of the bypass segment to the patient's anatomical structure. Alternatively, the tablet computer 70 may recommend where to connect the bypass segment at one or both ends of the bypass segment. The tablet computer 70 may allow the user to place more than one bypass segment in the model, and remove the bypass segment(s), as desired. The tablet computer 70 may also allow the user to provide inputs (e.g., similar to the inputs described above, such as swiping and pinching) to change the location or dimension (e.g., diameter, length, etc.) of the bypass segment.

Once the treatment option(s) have been selected by the user, the user may touch a calculate button 340, as shown in FIG. 4. When the user selects the calculate button 340, the tablet computer 70 recalculates the blood flow characteristic(s).

For example, referring back to FIG. 1, after the computer system 40 solves the equations 30 as described above, the computer system 40 may create and transmit to the tablet computer 70 a reduced-order (e.g., zero-dimensional or one-dimensional) model 60 for modeling various treatment options, in addition to (or instead of) the information 50 indicating the blood flow characteristics in the patient's current condition, as disclosed, for example, in U.S. Patent Application Publication No. 2012/0041739 entitled "Method And System For Patient-Specific Modeling Of Blood Flow," For example, the reduced-order model 60 may be a lumped parameter model or other simplified model of the patient's anatomy that may be used to determine information about the coronary blood flow in the patient without having to solve the more complex system of equations 30 described above. The reduced-order model 60 may be created using information extracted from the computed models 100 and 200 (e.g., the blood pressure, flow, or velocity information determined by solving the equations 30 described above).

After the user touches the calculate button 340, the tablet computer 70 may adjust the reduced-order model 60 based on the treatment option selected by the user, and may solve a simplified set of equations based on the reduced-order model 60 to output information indicating one or more predicted blood flow characteristics (e.g., FFR, blood pressure (or pressure gradient), etc.) of the patient. The information may then be mapped or extrapolated to the three-dimensional model 12 of the patient's anatomical structure to display the effects of the selected treatment option on the coronary blood flow in the patient's anatomy, e.g., in a post-intervention model 500, as shown in FIG. 6.

Since the reduced-order model 60 may be solved with a simplified set of equations (compared to the equations 30), the reduced-order model 60 permits relatively rapid computation (e.g., compared to a full three-dimensional model) using the tablet computer 70 and may be used to solve for flow rate and pressure that may closely approximate the results of a full three-dimensional computational solution. Thus, the reduced-order model 60 allows for relatively rapid iterations to model various different treatment options.

Alternatively, instead of creating the reduced-order model 60 and transmitting the reduced-order model 60 to the tablet computer 70, the inputs provided by the user to select the treatment option may be transmitted to the computer system 40 via the tablet computer 70 (e.g., via a wired or wireless connection). After the user touches the calculate button 340, the computer system 40 may recalculate the information indicating the blood flow characteristic(s), e.g., by re-solving the equations 30 using the inputs provided by the user to select the treatment option. The computer system 40 may then transmit to the tablet computer 70 the information indicating the blood flow characteristic(s) based on this solution to the equations 39, and may also output to the tablet computer 70 images generated based on the model 12 and the determined information, such as the post-intervention model 500 shown in FIG. 6.

FIG. 6 shows a screen shot of the tablet computer 70 operating in the second operating mode after determining the information indicating the blood flow characteristic(s) of the patient based on the selected treatment option, according to an embodiment. Specifically, the screen shot shows a split screen provided by touchscreen, and the split screen may divide the screen into two or more portions. In the embodiment shown in FIG. 6, two portions may be provided. The first portion of the split screen (the left side portion shown in FIG. 6) may show the pre-intervention model 400 (FIG. 4) with the treatment option selected by the user (placement of the stent 410, as described above in connection with FIG. 4).

The second portion of the split screen (the right side portion shown in FIG. 6) may show the post-intervention model 500 that reflects the information indicating the blood flow characteristic(s) of the patient based on selected treatment option. The post-intervention model 500 may show any change in geometry of the anatomical structure due to the selected treatment option. For example, in the embodiment shown in FIG. 6, the post-intervention model 500 shows a widening 510 of the lumen where the simulated stent 410 is placed. The post-intervention model 500 may also display the start and end points of the stent 410.

In the embodiment shown in FIG. 6, the pre-intervention and post-intervention models 400, 500 indicate computed FFR. The split screen allows the user to view and compare information relating to the untreated patient (e.g., without the stent(s)), such as the model 400, side-by-side with information relating to the simulated treatment for the patient, such as the model 500. For example, the same color, shade, pattern, or other visual indicators as the model 400 may be assigned to the respective FFR values for the model 500. Thus, the model 500 may also visually indicate the variations in FFR throughout the model 500 without having to specify the individual values for each point in the model 500. The model 500 shown in FIG. 6 shows that, for this particular patient, under the treatment plan selected by the user, FFR is generally uniform and approximately 1.0 in the aorta (e.g., as indicated by the color blue), and that FFR gradually and continuously decreases (e.g., to values ranging from 1.0 down to approximately 0.9, as indicated by gradually changing colors from blue to cyan or a mix of blue and cyan) in the main coronary arteries and the branches. In this embodiment, the post-interventional model 500 does not include the areas 112 and 114 of sharper decreases in FFR that are shown in the pre-interventional model 400. Thus, the split screen provides a comparison of the pre-interventional model 400 of the untreated patient (showing the patent's current condition) and the post-interventional model 500 for the proposed treatment to help the physician or other user to assess the results of various treatment options.

Either portion of the split screen may be configured to receive inputs from the user and may respond to the inputs as described above in connection with the first operating mode. For example, the user may touch any location on the model(s) 400 and/or 500 to determine the numerical value of any of the blood flow characteristic(s) and/or geometry information at that location, e.g., by creating one or more pins 330 for moving around the model(s) 400 and/or 500. In an embodiment, when the user touches a location (or creates the pin 330) on one of the models 400 or 500 to determine the numerical value of the blood flow characteristic(s) and/or geometry information at the indicated location, the numerical value of the blood flow characteristic(s) and/or geometry information at the same location in the other model 400 or 500 may also be displayed for comparison. For example, another pin 330 may be automatically created at the same location in the other model 400 or 500. As a result, the split screen may provide mirrored pins 330 in the two displayed models such that movement of one pin 330 in one of the models due to user input is automatically mirrored by the pin 330 in the other model and the numerical values of the blood flow characteristic(s) and/or geometry information at the respective locations may be compared and updated dynamically as the pins 330 move.

Also, the user may adjust the rotation, zoom, and/or focal point for the model(s) 400 and/or 500. In an embodiment, when the user adjusts the rotation, zoom, and/or focal point for one of the models 400 or 500, the rotation, zoom, and/or focal point for the other model 400 or 500 is adjusted similarly.

The first portion of the split screen (showing the pre-intervention model 400) may be configured to receive inputs from the user and may respond to the inputs as described above in connection with the second operating mode. For example, the user may select or adjust the treatment option using the pre-intervention model 400. After making the desired changes, the user may touch the calculate button 340, which may cause the tablet computer 70 to modify the reduced-order model 60 based on the new treatment option selected by the user. After solving the equations associated with the modified reduced-order model 60, the tablet computer 70 may output a modified post-intervention model 500 that reflects the new treatment option selected by the user. Alternatively, the tablet computer 70 may transmit the new treatment option to the computer system 40, which will re-solve the equations 30 based on the new selected treatment option, and send the modified post-intervention model 500 to the tablet computer 70 for displaying to the user.

Alternatively, the split screen may provide two portions for comparing the results of different treatment options. In such an embodiment, each portion of the split screen may be configured to receive inputs associated with selecting treatment options using the pre-intervention model 400 as described above and may be able to display different post-intervention models 500 based on the different treatment options selected.

Accordingly, the split screen allows the user to repeatedly select new treatment options and use the tablet computer 70 to predict and compare the effects of various treatment options to each other and/or to information relating to the untreated patient. The reduced-order model 60 may allow the user to analyze and compare different treatment options more easily and quickly without having to solve the equations 30 each time a different treatment option is selected.

The system may be used to predict a potential benefit of percutaneous coronary interventions on coronary artery blood flow in order to select the optimal interventional strategy, and/or to predict a potential benefit of coronary artery bypass grafting on coronary artery blood flow in order to select the optimal surgical strategy.

The systems and methods disclosed herein may be incorporated into a portable software tool accessed by physicians and other users to provide patient-specific blood flow information and to plan treatment options. In addition, physicians and other users may use the portable software tool to predict the effect of medical, interventional, and/or surgical treatments on coronary artery blood flow. The portable software tool may be used to prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The portable software tool may be interactive to enable physicians and other users to develop optimal personalized therapies for patients.

The computer system 40 for solving the equations 30 governing blood flow may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the patient-specific anatomical data 10 obtained noninvasively from the patient may be provided to the service provider, and the service provider may use the data to produce the three-dimensional model 12 or other models/meshes and/or any simulations or other results determined by solving the equations 30 described above in connection with FIG. 1, such as the reduced-order model 60, the computed FFR model 100, and/or the computed blood pressure gradient model 200. Then, the web-based service may transmit the models 60, 100, and/or 200 to the physician's tablet computer 70 (or other portable device). The physician may use the tablet computer 70 to interact with the models 100 or 200, and to provide inputs, e.g., to select possible treatment options and determine blood flow information based on the selected possible treatment options.

It will be apparent to those skilled in the art that various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A system for planning a treatment for a patient, the system comprising:
   at least one memory storing instructions;
   at least one display; and
   at least one processor operatively connected to the memory and configured to execute the instruction to perform operations, including:
      displaying, via a first portion of the at least one display, a first simulation result that includes a first three-dimensional (3D) anatomical model of a portion of a patient's vasculature in a pre-interventional first simulation condition;
      receiving a user selection of a treatment option for the patient; and
      displaying, while the first simulation result is being displayed by the first portion of the at least one display and via a second portion of the at least one display, a second simulation result that includes a second 3D anatomical model of the portion of the patient's vasculature in a post-interventional second simulation condition based on the selected treatment option;
   wherein:
      the at least one processor is further configured to receive a user interaction indicative of a modification to the selected treatment option; and
      in response to receiving the user interaction, the at least one processor is further configured to:
         cause the second simulation result to be updated based on the modification to the selected treatment option; and
         update the display of the second simulation result on the second portion of the at least one display.

2. The system of claim 1, wherein the at least one processor is further configured to display the first and second simulation results on the display based on a same reference point within the 3D anatomical model.

3. The system of claim 2, wherein the reference point corresponds to a stenosis.

4. The system of claim 1, wherein the at least one processor is further configured to display one or more evaluation criteria on the 3D anatomical model based on the first and second simulation results.

5. The system of claim 4, wherein the operations further include:
   displaying, via the display, a user menu that is configured to receive a further user selection to select the one or more evaluation criteria to be displayed on the display for the simulation results; and
   wherein the first and second simulation results are displayed based on the selected one or more evaluation criteria.

6. The system of claim 4, wherein the at least one processor is further configured to:
   receive a further user selection of a reference location at which numerical values of the one or more evaluation criteria are to be displayed; and
   display the numerical values of the one or more evaluation criteria on the 3D anatomical model, displayed as the first and second simulation results, at the reference location.

7. The system of claim 4, wherein the one or more evaluation criteria includes one or more of a fractional flow reserve (FFR) value, blood pressure, blood pressure gradient, or a velocity value.

8. The system of claim 1, wherein:
   the treatment option includes a placement of a stent; and
   the modification to the treatment option includes an adjustment to one or more of a characteristic of the stent or a position of the stent.

9. A method for planning a treatment for a patient, the method comprising:
   displaying, via a first portion of at least one display of a treatment planning system, a first simulation result that includes a first three-dimensional (3D) anatomical model of a portion of a patient's vasculature in a pre-interventional first simulation condition;
   receiving, via an input device of the treatment planning system, a user selection of a treatment option for the patient; and
   displaying, while the first simulation result is being displayed by the first portion of the at least one display and via a second portion of the at least one display, a second simulation result that includes a second 3D anatomical model of the portion of the patient's vasculature in a post-interventional second simulation condition based on the selected treatment option;
   receiving, via the input device, a user interaction indicative of a modification to the selected treatment option; and in response to receiving the user interaction:
cause the second simulation result to be updated based on the modification to the selected treatment option; and
update the display of the second simulation result on the second portion of the at least one display.

10. The method of claim 9, wherein the first and second simulation results are displayed on the display based on a same reference point within the 3D anatomical model.

11. The method of claim 10, wherein the reference point corresponds to a stenosis.

12. The method of claim 9, further comprising:
displaying one or more evaluation criteria on the 3D anatomical model based on the first and second simulation results.

13. The method of claim 12, further comprising:
displaying, via the display, a user menu that is configured to receive a further user selection to select the one or more evaluation criteria to be displayed on the display for the simulation results; and
receiving, via the input device, the further user selection of the one or more evaluation criteria,
wherein the first and second simulation results are displayed based on the selected one or more evaluation criteria.

14. The method of claim 12, further comprising:
receiving, via the input device, a further user selection of a reference location at which numerical values of the one or more evaluation criteria are to be displayed; and
displaying the numerical values of the one or more evaluation criteria on the 3D anatomical model, as the first and second simulation results, at the reference location.

15. The method of claim 12, wherein the one or more evaluation criteria includes one or more of a fractional flow reserve (FFR) value, blood pressure, blood pressure gradient, or a velocity value.

16. The method of claim 9, wherein:
the treatment option includes a placement of a stent; and
the modification to the treatment option includes an adjustment to one or more of a characteristic of the stent or a position of the stent.

17. A non-transitory computer readable medium for use on a computer system containing computer-executable programming instructions that are executable by a processor to perform operations, the operations comprising:
displaying, via a first portion of at least one display of a treatment planning system, a first simulation result that includes a first three-dimensional (3D) anatomical model of a portion of a patient's vasculature in a pre-interventional first simulation condition;
receiving, via an input device of the treatment planning system, a user selection of a treatment option for the patient;
displaying, while the first simulation result is being displayed by the first portion of the at least one display and via a second portion of the at least one display, a second simulation result that includes a second 3D anatomical model of the portion of the patient's vasculature in a post-interventional second simulation condition based on the selected treatment option;
receiving, via the input device, a user interaction indicative of a modification to the selected treatment option; and
in response to receiving the user interaction:
cause the second simulation result to be updated based on the modification to the selected treatment option; and
update the display of the second simulation result on the second portion of the at least one display.

18. The non-transitory computer readable medium of claim 17, wherein the first and second simulation results are displayed on the display based on a same reference point within the 3D anatomical model.

19. The non-transitory computer readable medium of claim 17, the operations further comprising:
displaying one or more evaluation criteria on the 3D anatomical model based on the first and second simulation results;
displaying, via the display, a user menu that is configured to receive a further user selection to select the one or more evaluation criteria to be displayed on the display for the simulation results; and
receiving, via the input device, the further user selection of the one or more evaluation criteria, wherein:
the first and second simulation results are displayed based on the selected one or more evaluation criteria; and
the one or more evaluation criteria includes one or more of a fractional flow reserve (FFR) value, blood pressure, blood pressure gradient, or a velocity value.

20. The non-transitory computer readable medium of claim 17, wherein:
the treatment option includes a placement of a stent; and
the modification to the treatment option includes an adjustment to one or more of a characteristic of the stent or a position of the stent.

* * * * *